United States Patent
Hirawat et al.

(10) Patent No.: US 10,213,432 B2
(45) Date of Patent: Feb. 26, 2019

(54) DOSAGE REGIMEN FOR A PI-3 KINASE INHIBITOR

(71) Applicant: NOVARTIS AG, Basel (CH)

(72) Inventors: Samit Hirawat, Chatham, NJ (US); Cristian Massacesi, Neuilly-sur-Seine (FR)

(73) Assignee: NOVARTIS AG, Basel (CH)

( * ) Notice: Subject to any disclaimer, the term of this patent is extended or adjusted under 35 U.S.C. 154(b) by 230 days.

(21) Appl. No.: 14/400,444

(22) PCT Filed: May 14, 2013

(86) PCT No.: PCT/US2013/040877
§ 371 (c)(1),
(2) Date: Nov. 11, 2014

(87) PCT Pub. No.: WO2013/173283
PCT Pub. Date: Nov. 21, 2013

(65) Prior Publication Data
US 2015/0141426 A1    May 21, 2015

Related U.S. Application Data

(60) Provisional application No. 61/647,654, filed on May 16, 2012.

(51) Int. Cl.
*A61K 31/505* (2006.01)
*A61K 31/506* (2006.01)
*A61K 31/5377* (2006.01)
*A61K 31/4196* (2006.01)

(52) U.S. Cl.
CPC ...... *A61K 31/5377* (2013.01); *A61K 31/4196* (2013.01)

(58) Field of Classification Search
CPC .......................... A61K 31/505; A61K 31/506
See application file for complete search history.

(56) References Cited

U.S. PATENT DOCUMENTS

| | | | | |
|---|---|---|---|---|
| 2005/0215795 A1* | 9/2005 | Chen | ............... | C07D 417/12 548/190 |
| 2010/0272717 A1* | 10/2010 | Evans | ............... | A61K 31/352 424/133.1 |
| 2010/0317661 A1* | 12/2010 | Wang | ............... | C07D 487/10 514/235.2 |

FOREIGN PATENT DOCUMENTS

| JP | 2009-527464 A | 7/2009 |
|---|---|---|
| JP | 2010-518107 A | 5/2010 |
| RU | 2448697 C2 | 3/2007 |
| WO | 2005/037341 A2 | 4/2005 |
| WO | 2006/080327 A1 | 3/2006 |
| WO | 2007/059106 A2 | 5/2007 |
| WO | 2007/084786 A1 | 7/2007 |
| WO | 2008018426 A1 | 2/2008 |
| WO | 2009/066084 A1 | 5/2009 |
| WO | 2010/044893 A1 | 4/2010 |

OTHER PUBLICATIONS

J. G. Cannon Chapter Nineteen in Burger's Medicinal Chemistry and Drug Discovery, Fifth Edition, vol. I: Principles and Practice, Wiley-Interscience 1995, pp. 783-802, 784.*
Bendell Johanna C et al: "Phase I, dose-escalation study of BKM120, an oral pan-class I PI3K inhibitor, in patients with advanced solid tumors", Journal of Clinical Oncology, American Society of Clinical Oncology, US, vol. 30, No. 3, pp. 282-290 Jan. 1, 2012 (Jan. 1, 2012).
Matthew T Burger et al: "Identification of NVP-BKM120 as a potent, selective, orally bioavailable class I PI3 Kinase inhibitor for treating cancer", ACS Medical Chemistry Letters, American Chemical Society, US, vol. 2, No. 10 Oct. 13, 2011 (Oct. 13, 2011), pp. 774-779.
Brachmann Saskia M et al: "Characertization of the mechanism of action of the pan class I PI3K inhibitor NVP-BKM120 across a broad range of concentrations", Molecular Cancer Therapeutics, vol. 11, No. 8, Aug. 2012 (Aug. 2012), pp. 1747-1757.
La Rosee Paul et al: "Weekend drug holiday of dasatinib in CML patients not tolerating standard dosing regimens. Reducing toxicity with maintained disease control", Blood, vol. 114, No. 22, Nov. 2009 (Nov. 2009), p. 459.
Maira et al: "Identification and characterization of NVP-BKM120, an orally available pan-class I PI3-Kinase inhibitor"; Molecular Cancer Therapeutics, vol. 11, No. 2, pp. 317-328 Jan. 2, 2012 (Jan. 2, 2012).
Matthew T Burger et al: "Synthesis and in vitro and in vivo evaluation of phosphoinositide-3-kinase inhibitors", ACS Medical Chemistry Letters, American Chemical Society, US, vol. 2, No. 1, pp. 34-38.
Cesar G Sanchez et al: "Preclinical modeling of combined phosphatidylinositol-3-kinase inhibition with endocrine for therapy estrogen receptor-positive breast cancer", Breast Cancer Research 2011, vol. 13, No. 2, pp. 1-17, 2011.
Solaro Sadahior, et al: "Two patients with recurrent colon cancer who underwent surgery following a combination of irinotecan and UFT", Cancer and Chemotherpy, vol. 29(11) :2013-2018, Nov. 2002.
Masato Nomura, et al: "Th1/Th2 in Neoadjuvant chemotherapy for esophageal cancer", Biotheraphy, Jan. 30, 2003, vol. 17, No. 1, p. 20-25.
Hiroichiro Suzuki, et al: Trial of outpatient anti-cancer chemotherapy with infusion of 5-FU and cisplatin for advanced gastric and colorectal cancers, Cancer and Chemotheraphy, Feb. 15, 2005, vol. 32, No. 2, p. 189-193.

(Continued)

*Primary Examiner* — Kendra D Carter
(74) *Attorney, Agent, or Firm* — Hoxie & Associates LLC

(57) ABSTRACT

The present invention relates to a dosage regimen for a phosphatidylinositol 3-kinase (PI3K) inhibitor compound of formula (I) or a pharmaceutically acceptable salt thereof. More specifically, the present invention relates to a dosage regimen for the treatment of patients suffering from a proliferative disease, such as, for example, cancer, with a phosphatidylinositol 3-kinase (PI3K) inhibitor compound of formula (I) or a pharmaceutically acceptable salt thereof.

2 Claims, No Drawings

(56) References Cited

OTHER PUBLICATIONS

Taishi Hata: "Case Report—Complete response of liver metasiasis of rectal cancer after combination chemotheraphy of CPT-11 4-UFT-E", Cancer and Chemotheraphy, Oct. 31, 2004, vol. 31, No. 11, p. 1702-1704.
Alimta, Instructions for Use, Registration No. LC-000355, date of registration Jun. 3, 2005, retrieved on Dec. 14, 2016 from the internet: http://medistok.ru/a/I119-alimta-instrukciia-po-primeneuiiu.htmn.
Tokunaga, Y, "Compliance of 5-day-on/2-day-off UFT/Leucovorin in Long-term Adjuvant Chemotherapy for Colorectal Cancer", Deaprtmentof Surgery, Journal of Japanese College of Surgeons, Feb. 29, 2012, vol. 37, No. 1, pp. 20-23 [English Abstract].
Mayer et al., "Stand Up to Cancer Phase Ib Study of Pan-Phosphoinositide-3-Kinase Inhibitor Buparlisib With Letrozole in Estrogen Receptor-Positive/Human Epidermal Growth Factor Receptor 2-Negative Metastatic Breast Cancer", Journl of Clinical Oncology, vol. 3, No. 12, Apr. 20, 2014.

* cited by examiner

DOSAGE REGIMEN FOR A PI-3 KINASE INHIBITOR

FIELD OF THE INVENTION

The present invention relates to a dosage regimen for a phosphatidylinositol 3-kinase (PI-3 kinase) inhibitor compound of formula (I) or a pharmaceutically acceptable salt thereof. More specifically, the present invention relates to a dosage regimen for the treatment of patients suffering from a proliferative disease, such as, for example, cancer, with a phosphatidylinositol 3-kinase (PI-3 kinase) inhibitor compound of formula (I) or a pharmaceutically acceptable salt thereof.

BACKGROUND OF THE INVENTION

Phosphatidylinositol 3-kinases (PI-3 kinase or PI3K) comprise a family of lipid and serine/threonine kinases that catalyze the transfer of phosphate to the D-3' position of inositol lipids to produce phosphoinositol-3-phosphate (PIP), phosphoinositol-3,4-diphosphate (PIP2) and phosphoinositol-3,4,5-triphosphate (PIP3) that, in turn, act as second messengers in signaling cascades by docking proteins containing pleckstrin-homology, FYVE, Phox and other phospholipid-binding domains into a variety of signaling complexes often at the plasma membrane ((Vanhaesebroeck et al., Annu. Rev. Biochem 70:535 (2001); Katso et al., Annu. Rev. Cell Dev. Biol. 17:615 (2001)). Of the two Class 1 PI3Ks, Class 1A PI3Ks are heterodimers composed of a catalytic p110 subunit ($\alpha$, $\beta$, $\delta$ isoforms) constitutively associated with a regulatory subunit that can be p85$\alpha$, p55$\alpha$, p50$\alpha$, p85$\beta$ or p55$\gamma$. The Class 1B sub-class has one family member, a heterodimer composed of a catalytic p110$\gamma$ subunit associated with one of two regulatory subunits, p101 or p84 (Fruman et al., Annu Rev. Biochem. 67:481 (1998); Suire et al., Curr. Biol. 15:566 (2005)). The modular domains of the p85/55/50 subunits include Src Homology (SH2) domains that bind phosphotyrosine residues in a specific sequence context on activated receptor and cytoplasmic tyrosine kinases, resulting in activation and localization of Class 1A PI3Ks. Class 1B PI3K is activated directly by G protein-coupled receptors that bind a diverse repertoire of peptide and non-peptide ligands (Stephens et al., Cell 89:105 (1997)); Katso et al., Annu. Rev. Cell Dev. Biol. 17:615-675 (2001)). Consequently, the resultant phospholipid products of class I PI3K link upstream receptors with downstream cellular activities including proliferation, survival, chemotaxis, cellular trafficking, motility, metabolism, inflammatory and allergic responses, transcription and translation (Cantley et al., Cell 64:281 (1991); Escobedo and Williams, Nature 335:85 (1988); Fantl et al., Cell 69:413 (1992)).

PI-3 kinase inhibitors are useful therapeutic compounds for the treatment of various conditions in humans. Aberrant regulation of PI3K, which often increases survival through Akt activation, is one of the most prevalent events in human cancer and has been shown to occur at multiple levels. The tumor suppressor gene PTEN, which dephosphorylates phosphoinositides at the 3' position of the inositol ring and in so doing antagonizes PI3K activity, is functionally deleted in a variety of tumors. In other tumors, the genes for the p110$\alpha$ isoform, PIK3CA, and for Akt are amplified and increased protein expression of their gene products has been demonstrated in several human cancers. Furthermore, mutations and translocation of p85$\alpha$ that serve to up-regulate the p85-p110 complex have been described in a few human cancers. Finally, somatic missense mutations in PIK3CA that activate downstream signaling pathways have been described at significant frequencies in a wide diversity of human cancers (Kang et al., Proc. Natl. Acad. Sci. USA 102:802 (2005); Samuels et al., Science 304:554 (2004); Samuels et al., Cancer Cell 7:561-573 (2005)). These observations show that deregulation of phosphoinositol-3 kinase and the upstream and downstream components of this signaling pathway is one of the most common deregulations associated with human cancers and proliferative diseases (Parsons et al., Nature 436:792 (2005); Hennessey at el., Nature Rev. Drug Dis. 4:988-1004 (2005)).

The efficacy of the PI-3 kinase inhibitor compound 5-(2, 6-di-morpholin-4-yl-pyrimidin-4-yl)-4-trifluoromethyl-pyridin-2-ylamine (also known as BKM120) in the treatment of solid tumors has been demonstrated in humans. Bendell et al., J. Clin. Oncology (2012 Jan. 20), 30(3): 282-90.

PI-3 kinase inhibitors may produce a negative side effect, including but not limited to, mood alteration, hyperglycemia, rash, diarrhea, anorexia, nausea, fatigue, pruritus and mucositis, at therapeutic doses. Daily administration of 100 mg of BKM120 to human patients in need thereof may induce such negative side effects as described in Bendell et al., J. Clin. Oncology (2012 Jan. 20), 30(3): 282-90.

There is a need, with respect to drugs that are PI3K inhibitors, as there is with drugs in general, to administer the drugs to patients in the lowest efficacious amount, so as to minimize any known side effects of the drug, as well as any unknown side effects.

SUMMARY OF THE INVENTION

This invention relates to a method of treating a proliferative disease in a human patient in need of such treatment, comprising administering to said patient a compound of formula (I) or a pharmaceutically acceptable salt thereof in a therapeutically effective amount of about 60 to about 120 mg daily for five consecutive days in any seven day period.

In a further embodiment, the invention relates to a method of treating a proliferative disease comprising first administering to a human patient in need thereof a compound of formula (I) or a pharmaceutically acceptable salt thereof in a therapeutically effective amount of about 60 to about 120 mg daily, second determining said patient has a condition selected from neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis. after administration of the compound of formula (I) or a pharmaceutically acceptable salt thereof after administration of about 60 mg to about 120 mg daily to said human patient, and third reducing the dosage of the compound of formula (I) or a pharmaceutically acceptable salt thereof to about 60 mg to about 120 mg daily for five consecutive days in any seven day period.

Use of a compound of formula (I) or a pharmaceutically acceptable salt thereof in the preparation of a medicament for use in the treatment of a proliferative disease wherein the medicament comprises about 60 to about 120 mg of compound of formula (I) is administered to a human patient in need thereof for five consecutive days in any seven day period.

Use of a compound of formula (I) or a pharmaceutically acceptable salt thereof for use in the treatment of a proliferative disease comprising administering about 60 to about 120 mg of compound of formula (I) or a pharmaceutically acceptable salt thereof for five consecutive days in any seven day period.

A therapeutic regimen comprising administering a compound of formula (I) or a pharmaceutically acceptable salt thereof in a therapeutically effective amount of about 60 to about 120 mg of compound of formula (I) or a pharmaceutically acceptable salt thereof for five consecutive days in any seven day period and wherein the compound of formula (I) or a pharmaceutically acceptable salt thereof is administered in combination with at least one additional therapeutic agent.

A pharmaceutical composition for use in the treatment of a proliferative disease in a human patient in need thereof comprising a therapeutically effective amount of about 60 to about 120 mg of a compound of formula (I) or pharmaceutically acceptable salt thereof together with one or more pharmaceutically acceptable excipients which is administered for five consecutive days in any seven day period.

A package comprising the pharmaceutical composition comprising a compound of formula (I) or a pharmaceutically acceptable salt thereof together with one or more pharmaceutically acceptable pharmaceutically acceptable excipients in combination with instructions to administer said composition in an amount of about 60 mg to about 120 mg of a compound of formula (I) or a pharmaceutically acceptable salt thereof for five consecutive days in any seven day period.

DETAILED DESCRIPTION OF THE INVENTION

This invention relates to a method of treating a proliferative disease in a human patient in need of such treatment, comprising administering to the patient a compound of formula (I) or a pharmaceutically acceptable salt thereof in a therapeutically effective amount of about 60 to about 120 mg daily for five consecutive days in any seven day period.

The general terms used herein are defined with the following meanings, unless explicitly stated otherwise:

The terms "comprising" and "including" are used herein in their open-ended and non-limiting sense unless otherwise noted.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "a phosphatidylinositol 3-kinase inhibitor" or "PI3K inhibitor" is defined herein to refer to a compound which targets, decreases or inhibits PI 3-kinase. PI 3-kinase activity has been shown to increase in response to a number of hormonal and growth factor stimuli, including insulin, platelet-derived growth factor, insulin-like growth factor, epidermal growth factor, colony-stimulating factor, and hepatocyte growth factor, and has been implicated in processes related to cellular growth and transformation.

"Alkyl" refers to alkyl groups that do not contain heteroatoms. Thus the phrase includes straight chain alkyl groups such as methyl, ethyl, propyl, butyl, pentyl, hexyl, heptyl, octyl, nonyl, decyl, undecyl, dodecyl and the like. The phrase also includes branched chain isomers of straight chain alkyl groups, including but not limited to, the following which are provided by way of example: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)—CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH$_2$CH$_2$C(CH$_2$CH$_3$)$_3$, —CH(CH$_3$)CH$_2$—CH(CH$_3$)$_2$, —CH(CH$_3$)CH(CH$_3$)CH(CH$_3$)$_2$, —CH(CH$_2$CH$_3$)CH(CH$_3$)CH(CH$_3$)(CH$_2$CH$_3$), and others. Thus the phrase "alkyl groups" includes primary alkyl groups, secondary alkyl groups, and tertiary alkyl groups. Preferred alkyl groups include straight and branched chain alkyl groups having 1 to 12 carbon atoms or 1 to 6 carbon atoms.

"Alkylene" refers to the same residues as noted above for "alkyl," but having two points of attachment. Exemplary alkylene groups include ethylene (—CH$_2$CH$_2$—), propylene (—CH$_2$CH$_2$CH$_2$—), dimethylpropylene (—CH$_2$C(CH$_3$)$_2$CH$_2$—), and cyclohexylpropylene (—CH$_2$CH$_2$CH(C$_6$H$_{13}$)—).

"Alkenyl" refers to straight chain, branched, or cyclic groups from 2 to about 20 carbon atoms such as those described with respect to alkyl groups as defined above, except having one or more carbon-carbon double bonds. Examples include, but are not limited to vinyl, —CH═C(H)(CH$_3$), —CH═C(CH$_3$)$_2$, —C(CH$_3$)═C(H)$_2$, —C(CH$_3$)═C(H)(CH$_3$), —C(CH$_2$CH$_3$)═CH$_2$, cyclohexenyl, cyclopentenyl, cyclohexadienyl, butadienyl, pentadienyl, and hexadienyl among others. Preferred alkenyl groups include straight chain and branched alkenyl groups and cyclic alkenyl groups having 2 to 12 carbon atoms or 2 to 6 carbon atoms.

"Alkynyl" refers to straight chain, branched, or cyclic groups from 2 to about 20 carbon atoms such as those described with respect to alkyl groups as defined above, except having one or more carbon-carbon triple bonds. Examples include, but are not limited to —C≡C(H), —C≡C(CH$_3$), —C≡C(CH$_2$CH$_3$), —C(H$_2$)CC(H), —C(H)$_2$C≡C(CH$_3$), and —C(H)$_2$C≡C(CH$_2$CH$_3$) among others. Preferred alkynyl groups include straight chain and branched alkynyl groups having 2 to 12 carbon atoms or 2 to 6 carbon atoms.

Alkyl, alkenyl, and alkynyl groups may be substituted. "Substituted alkyl" refers to an alkyl group as defined above in which one or more bonds to a carbon(s) or hydrogen(s) are replaced by a bond to non-hydrogen and non-carbon atoms such as, but not limited to, a halogen atom such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a higher-order bond (e.g., a double- or triple-bond) to a heteroatom such as oxygen in oxo, carbonyl, carboxyl, and ester groups; nitrogen in groups such as imines, oximes, hydrazones, and nitriles. Substituted alkyl groups further include alkyl groups in which one or more bonds to a carbon(s) or hydrogen(s) atoms is replaced by a bond to an aryl, heteroaryl, heterocyclyl, or cycloalkyl group. Preferred substituted alkyl groups include, among others, alkyl groups in which one or more bonds to a carbon or hydrogen atom is/are replaced by one or more bonds to fluoro, chloro, or bromo group. Another preferred substituted alkyl group is the trifluoromethyl group and other alkyl groups that contain the trifluoromethyl group. Other preferred substituted alkyl groups include those in which one or more bonds to a carbon or hydrogen atom is replaced by a bond to an oxygen atom such that the substituted alkyl group contains a hydroxyl, alkoxy, or aryloxy group. Other preferred substituted alkyl groups include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other preferred substituted alkyl groups include those in which one or more bonds to a carbon(s) or hydrogen(s) atoms is replaced by a bond to an aryl, heteroaryl, heterocyclyl, or cycloalkyl group. Examples of substituted alkyl are: —(CH$_2$)$_3$NH$_2$, —(CH$_2$)$_3$NH(CH$_3$), —(CH$_2$)$_3$NH(CH$_3$)$_2$, —CH$_2$C(=CH$_2$) CH$_2$NH$_2$, —CH$_2$C(=O)CH$_2$NH$_2$, —CH$_2$S(=O)$_2$CH$_3$, —CH$_2$OCH$_2$NH$_2$, —CO$_2$H. Examples of substituents of substituted alkyl are: —CH$_3$, —C$_2$H$_5$, —CH$_2$OH, —OH, —OCH$_3$, —OC$_2$H$_5$, —OCF$_3$, —OC(=O)CH$_3$, —OC(=O) NH$_2$, —OC(=O)N(CH$_3$)$_2$, —CN, —NO$_2$, —C(=O)CH$_3$, —CO$_2$H, —CO$_2$CH$_3$, —CONH$_2$, —NH$_2$, —N(CH$_3$)$_2$, —NHSO$_2$CH$_3$, —NHCOCH$_3$, —NHC(=O)OCH$_3$, —NHSO—$_2$CH$_3$, —SO$_2$CH$_3$, —SO$_2$NH$_2$, Halo.

"Substituted alkenyl" has the same meaning with respect to alkenyl groups that substituted alkyl groups had with respect to unsubstituted alkyl groups. A substituted alkenyl group includes alkenyl groups in which a non-carbon or non-hydrogen atom is bonded to a carbon double bonded to another carbon and those in which one of the non-carbon or non-hydrogen atoms is bonded to a carbon not involved in a double bond to another carbon.

"Substituted alkynyl" has the same meaning with respect to alkynyl groups that substituted alkyl groups had with respect to unsubstituted alkyl groups. A substituted alkynyl group includes alkynyl groups in which a non-carbon or non-hydrogen atom is bonded to a carbon triple bonded to another carbon and those in which a non-carbon or non-hydrogen atom is bonded to a carbon not involved in a triple bond to another carbon.

"Alkoxy" refers to RO— wherein R is alkyl. Representative examples of alkoxy groups include methoxy, ethoxy, t-butoxy, trifluoromethoxy, and the like.

"Halogen" or "halo" refers to chloro, bromo, fluoro, and iodo groups. The term "haloalkyl" refers to an alkyl radical substituted with one or more halogen atoms. The term "haloalkoxy" refers to an alkoxy radical substituted with one or more halogen atoms.

"Amino" refers herein to the group —NH$_2$. The term "alkylamino" refers herein to the group —NRR' where R is alkyl and R' is hydrogen or alkyl. The term "arylamino" refers herein to the group —NRR' where R is aryl and R' is hydrogen, alkyl, or aryl. The term "aralkylamino" refers herein to the group —NRR' where R is aralkyl and R' is hydrogen, alkyl, aryl, or aralkyl.

"Alkoxyalkyl" refers to the group -alk$_1$-O-alk$_2$ where alk$_1$ is alkyl or alkenyl, and alk$_2$ is alkyl or alkenyl. The term "aryloxyalkyl" refers to the group -alkyl O-aryl. The term "aralkoxyalkyl" refers to the group -alkylenyl-O-aralkyl.

"Alkoxyalkylamino" refers herein to the group —NR-(alkoxyalkyl), where R is typically hydrogen, aralkyl, or alkyl.

"Aminocarbonyl" refers herein to the group —C(O)—NH$_2$. "Substituted aminocarbonyl" refers herein to the group —C(O)—NRR' where R is alkyl and R' is hydrogen or alkyl. The term "arylaminocarbonyl" refers herein to the group —C(O)—NRR' where R is aryl and R' is hydrogen, alkyl or aryl. "Aralkylaminocarbonyl" refers herein to the group —C(O)—NRR' where R is aralkyl and R' is hydrogen, alkyl, aryl, or aralkyl.

"Aminosulfonyl" refers herein to the group —S(O)$_2$—NH$_2$. "Substituted aminosulfonyl" refers herein to the group —S(O)$_2$—NRR' where R is alkyl and R' is hydrogen or alkyl. The term "aralkylaminosulfonlyaryl" refers herein to the group -aryl-S(O)$_2$—NH-aralkyl.

"Carbonyl" refers to the divalent group —C(O)—.

"Carbonyloxy" refers generally to the group —C(O)—O. Such groups include esters, —C(O)—O—R, where R is alkyl, cycloalkyl, aryl, or aralkyl. The term "carbonyloxycycloalkyl" refers generally herein to both a "carbonyloxycarbocycloalkyl" and a "carbonyloxyheterocycloalkyl," i.e., where R is a carbocycloalkyl or heterocycloalkyl, respectively. The term "arylcarbonyloxy" refers herein to the group —C(O)—O-aryl, where aryl is a mono- or polycyclic, carbocycloaryl or heterocycloaryl. The term "aralkylcarbonyloxy" refers herein to the group —C(O)—O-aralkyl.

"Sulfonyl" refers herein to the group —SO$_2$—. "Alkylsulfonyl" refers to a substituted sulfonyl of the structure —SO$_2$R— in which R is alkyl. Alkylsulfonyl groups employed in compounds of the present invention are typically alkylsulfonyl groups having from 1 to 6 carbon atoms in its backbone structure. Thus, typical alkylsulfonyl groups employed in compounds of the present invention include, for example, methylsulfonyl (i.e., where R is methyl), ethylsulfonyl (i.e., where R is ethyl), propylsulfonyl (i.e., where R is propyl), and the like. The term "arylsulfonyl" refers herein to the group —SO$_2$-aryl. The term "aralkylsulfonyl" refers herein to the group —SO$_2$-aralkyl. The term "sulfonamido" refers herein to —SO$_2$NH$_2$.

"Carbonylamino" refers to the divalent group —NH—C(O)— in which the hydrogen atom of the amide nitrogen of the carbonylamino group can be replaced alkyl, aryl, or aralkyl group. Such groups include moieties such as carbamate esters (—NH—C(O)—O—R) and amides —NH—C(O)—R, where R is a straight or branched chain alkyl, cycloalkyl, or aryl or aralkyl. The term "alkylcarbonylamino" refers to alkylcarbonylamino where R is alkyl having from 1 to about 6 carbon atoms in its backbone structure. The term "arylcarbonylamino" refers to group —NH—C(O)—R where R is an aryl. Similarly, the term "aralkylcarbonylamino" refers to carbonylamino where R is aralkyl.

"Cycloalkyl" refers to a mono- or polycyclic, heterocyclic or carbocyclic alkyl substituent. Representative cycloalkyl groups include cyclopropyl, cyclobutyl, cyclopentyl, cyclohexyl, cycloheptyl, and cyclooctyl and such rings substituted with straight and branched chain alkyl groups as defined above. Typical cycloalkyl substituents have from 3 to 8 backbone (i.e., ring) atoms in which each backbone atom is either carbon or a heteroatom. The term "heterocycloalkyl" refers herein to cycloalkyl substituents that have from 1 to 5, and more typically from 1 to 4 heteroatoms in the ring structure. Suitable heteroatoms employed in compounds of the present invention are nitrogen, oxygen, and sulfur. Representative heterocycloalkyl moieties include, for example, morpholino, piperazinyl, piperadinyl, and the like. Carbocycloalkyl groups are cycloalkyl groups in which all ring atoms are carbon. When used in connection with cycloalkyl substituents, the term "polycyclic" refers herein to fused and non-fused alkyl cyclic structures.

"Substituted heterocycle," "heterocyclic group," "heterocycle," or "heterocyclyl," as used herein refers to any 3- or 4-membered ring containing a heteroatom selected from nitrogen, oxygen, and sulfur or a 5- or 6-membered ring containing from one to three heteroatoms selected from the group consisting of nitrogen, oxygen, or sulfur; wherein the 5-membered ring has 0-2 double bonds and the 6-membered ring has 0-3 double bonds; wherein the nitrogen and sulfur atom maybe optionally oxidized; wherein the nitrogen and sulfur heteroatoms maybe optionally quarternized; and including any bicyclic group in which any of the above heterocyclic rings is fused to a benzene ring or another 5- or 6-membered heterocyclic ring independently defined above. Examples of heterocyclyl groups include, but are not limited to: unsaturated 3- to 8-membered rings containing 1 to 4 nitrogen atoms such as, but not limited to pyrrolyl, dihydropyridyl, pyrimidyl, pyrazinyl, tetrazolyl, (e.g., 1H-tetrazolyl, 2H-tetrazolyl); condensed unsaturated heterocyclic groups containing 1 to 4 nitrogen atoms such as, but not limited to, isoindolyl, indolinyl, indolizinyl, quinolyl, indazolyl; unsaturated 3- to 8-membered rings containing 1 to 2 oxygen atoms and 1 to 3 nitrogen atoms such as, but not limited to, oxadiazolyl (e.g., 1,2,4-oxadiazolyl, 1,3,4-oxadiazolyl, 1,2,5-oxadiazolyl); saturated 3- to 8-membered rings containing 1 to 2 oxygen atoms and 1 to 3 nitrogen atoms such as, but not limited to, morpholinyl; unsaturated condensed heterocyclic groups containing 1 to 2 oxygen atoms and 1 to 3 nitrogen atoms, for example, benzoxadiazolyl, benzoxazinyl (e.g., 2H-1,4-benzoxazinyl); unsaturated 3- to 8-membered rings containing 1 to 3 sulfur atoms and 1 to 3 nitrogen atoms such as, but not limited to, thiadiazolyl (e.g., 1,2,3-thiadiazolyl, 1,2,4-thiadiazolyl, 1,3,4-thiadiazolyl, 1,2,-thiadiazolyl); saturated 3- to 8-membered rings containing 1 to 2 sulfur atoms and 1 to 3 nitrogen atoms such as, but not limited to, thiazolodinyl; saturated and unsaturated 3- to 8-membered rings containing 1 to 2 sulfur atoms such as, but not limited to, dihydrodithienyl, dihydrodithionyl, tetrahydrothiophene, tetra-hydrothiopyran; unsaturated condensed heterocyclic rings containing 1 to 2 sulfur atoms and 1 to 3 nitrogen atoms such as, but not limited to, benzothiadiazolyl, benzothiazinyl (e.g., 2H-1,4-benzothiazinyl), dihydrobenzothiazinyl (e.g., 2H-3,4-dihydrobenzothiazinyl), unsaturated 3- to 8-membered rings containing oxygen atoms such as, but not limited to furyl; unsaturated condensed heterocyclic rings containing 1 to 2 oxygen atoms such as benzodioxoyl (e.g., 1,3-benzodioxoyl); unsaturated 3- to 8-membered rings containing an oxygen atom and 1 to 2 sulfur atoms such as, but not limited to, dihydrooxathienyl; saturated 3- to 8-membered rings containing 1 to 2 oxygen atoms and 1 to 2 sulfur atoms such as 1,4-oxathiane; unsaturated condensed rings containing 1 to 2 sulfur atoms such as benzodithienyl; and unsaturated condensed heterocyclic rings containing an oxygen atom and 1 to 2 oxygen atoms such as benzoxathienyl. Preferred heterocycles include, for example: diazapinyl, pyrryl, pyrrolinyl, pyrrolidinyl, pyrazolyl, pyrazolinyl, pyrazolidinyl, imidazoyl, imidazolinyl, imidazolidinyl, pyridyl, piperidinyl, pyrazinyl, piperazinyl, N-methyl piperazinyl, azetidinyl, N-methylazetidinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, triazolyl, and benzothienyl. Heterocyclyl groups also include those described above in which one or more S atoms in the ring is double-bonded to one or two oxygen atoms (sulfoxides and sulfones). For example, heterocyclyl groups include tetrahydrothiophene, tetrahydrothiophene oxide, and tetrahydrothiophene 1,1-dioxide. Preferred heterocyclyl groups contain 5 or 6 ring members. More preferred heterocyclyl groups include piperazine, 1,2, 3-triazole, 1,2,4-triazole, tetrazole, thiomorpholine, homopiperazine, oxazolidin-2-one, pyrrolidin-2-one, quinuclidine, and tetrahydrofuran.

Heterocyclic moieties can be unsubstituted or monosubstituted or disubstituted with various substituents independently selected from hydroxy, halo, oxo (C=O), alkylimino (RN=, wherein R is alkyl or alkoxy group), amino, alkylamino, dialkylamino, acylaminoalkyl, alkoxy, thioalkoxy, polyalkoxy, alkyl, cycloalkyl or haloalkyl. "Unsubstituted heterocyclyl" includes condensed heterocyclic rings such as benzimidazolyl, it does not include heterocyclyl groups that have other groups such as alkyl or halo groups bonded to one of the ring members as compounds such as 2-methylbenzimidazolyl are substituted heterocyclyl groups.

The heterocyclic groups may be attached at various positions as will be apparent to those having skill in the organic and medicinal chemistry arts in conjunction with the disclosure herein.

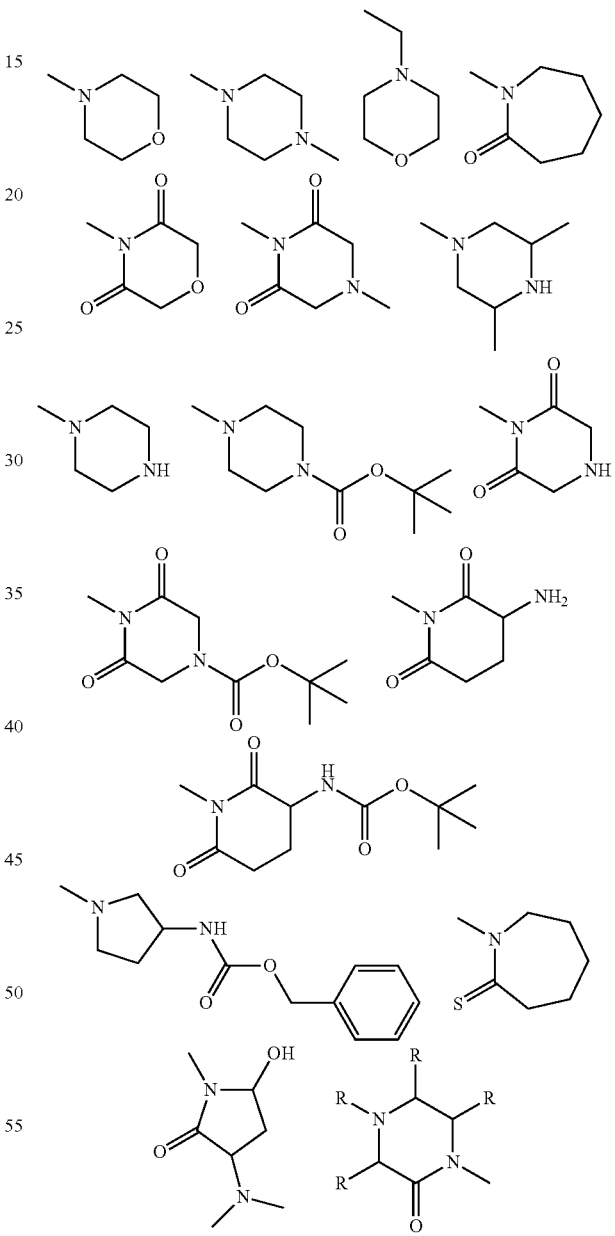

where R is H or a heterocyclic substituent, as described herein.

Representative heterocyclics include, for example, imidazolyl, pyridyl, piperazinyl, azetidinyl, thiazolyl, furanyl, triazolyl benzimidazolyl, benzothiazolyl, benzoxazolyl, quinolinyl, isoquinolinyl, quinazolinyl, quinoxalinyl, phthalazinyl, indolyl, naphthpyridinyl, indazolyl, and quinolizinyl.

"Aryl" refers to optionally substituted monocyclic and polycyclic aromatic groups having from 3 to 14 backbone carbon or hetero atoms, and includes both carbocyclic aryl groups and heterocyclic aryl groups. The term refers to, but is not limited to, groups such as phenyl, biphenyl, anthracenyl, naphthenyl by way of example. Carbocyclic aryl groups are aryl groups in which all ring atoms in the aromatic ring are carbon. The term "heteroaryl" refers herein to aryl groups having from 1 to 4 heteroatoms as ring atoms in an aromatic ring with the remainder of the ring atoms being carbon atoms.

"Unsubstituted aryl" includes groups containing condensed rings such as naphthalene. It does not include aryl groups that have other groups such as alkyl or halo groups bonded to one of the ring members, as aryl groups such as tolyl are considered herein to be substituted aryl groups as described below. A preferred unsubstituted aryl group is phenyl. Unsubstituted aryl groups may be bonded to one or more carbon atom(s), oxygen atom(s), nitrogen atom(s), and/or sulfur atom(s) in the parent compound, however.

"Substituted aryl group" has the same meaning with respect to unsubstituted aryl groups that substituted alkyl groups had with respect to unsubstituted alkyl groups. However, a substituted aryl group also includes aryl groups in which one of the aromatic carbons is bonded to one of the non-carbon or non-hydrogen atoms described above and also includes aryl groups in which one or more aromatic carbons of the aryl group is bonded to a substituted and/or unsubstituted alkyl, alkenyl, or alkynyl group as defined herein. This includes bonding arrangements in which two carbon atoms of an aryl group are bonded to two atoms of an alkyl, alkenyl, or alkynyl group to define a fused ring system (e.g., dihydronaphthyl or tetrahydronaphthyl). Thus, the phrase "substituted aryl" includes, but is not limited to tolyl, and hydroxyphenyl among others.

"Substituted heteroaryl" as used herein refers to a heteroaryl group as defined herein substituted by independent replacement of one, two or three of the hydrogen atoms thereon with Cl, Br, F, I, —OH, —CN, $C_1$-$C_3$-alkyl, $C_1$-$C_6$-alkoxy, $C_1$-$C_6$-alkoxy substituted with aryl, haloalkyl, thioalkoxy, amino, alkylamino, dialkylamino, mercapto, nitro, carboxaldehyde, carboxy, alkoxycarbonyl and carboxamide. In addition, any one substituent may be an aryl, heteroaryl, or heterocycloalkyl group.

When used in connection with aryl substituents, the term "polycyclic aryl" refers herein to fused and non-fused cyclic structures in which at least one cyclic structure is aromatic, such as, for example, benzodioxole (which has a heterocyclic structure fused to a phenyl group, i.e.,

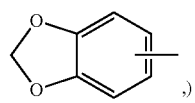

,)

naphthyl, and the like. Exemplary aryl or heteroaryl moieties employed as substituents in compounds of the present invention include phenyl, pyridyl, pyrimidinyl, thiazolyl, indolyl, imidazolyl, oxadiazolyl, tetrazolyl, pyrazinyl, triazolyl, thiophenyl, furanyl, quinolinyl, purinyl, naphthyl, benzothiazolyl, benzopyridyl, and benzimidazolyl, and the like.

"Aralkyl" or "arylalkyl" refers to an alkyl group substituted with an aryl group. Typically, aralkyl groups employed in compounds of the present invention have from 1 to 6 carbon atoms incorporated within the alkyl portion of the aralkyl group. Suitable aralkyl groups employed in compounds of the present invention include, for example, benzyl, picolyl, and the like.

Representative heteroaryl groups include, for example, those shown below. These heteroaryl groups can be further substituted and may be attached at various positions as will be apparent to those having skill in the organic and medicinal chemistry arts in conjunction with the disclosure herein.

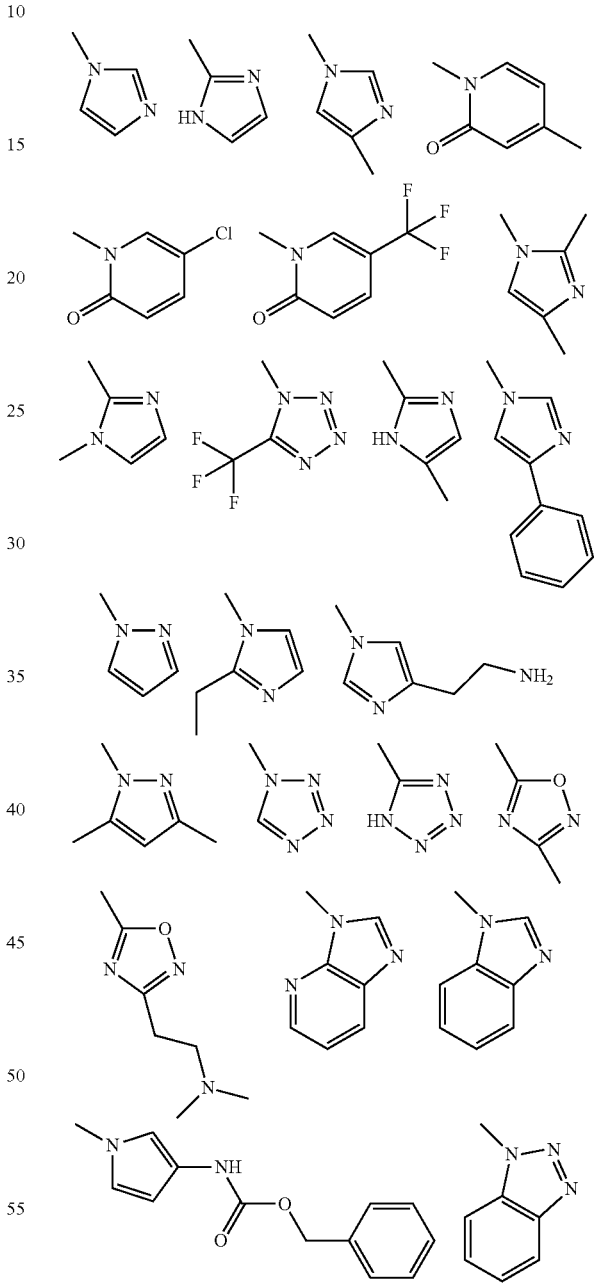

Representative heteroaryls include, for example, imidazolyl, pyridyl, thiazolyl, triazolyl benzimidazolyl, benzothiazolyl, and benzoxazolyl.

"Biaryl" refers to a group or substituent to which two aryl groups, which are not condensed to each other, are bound. Exemplary biaryl compounds include, for example, phenylbenzene, diphenyldiazene, 4-methylthio-1-phenylbenzene, phenoxybenzene, (2-phenylethynyl)benzene, diphenyl ketone, (4-phenylbuta-1,3-diynyl)benzene, phenylbenzylamine, (phenylmethoxy)benzene, and the like. Preferred optionally substituted biaryl groups include: 2-(phenylamino)-N-[4-(2-phenylethynyl)-phenyl]acetamide, 1,4-diphenylbenzene, N-[4-(2-phenylethynyl)phenyl]-2-[benzyl-amino]-acetamide, 2-amino-N-[4-(2-phenylethynyl)phenyl]propanamide, 2-amino-N-[4-(2-phenyl-ethynyl)phenyl]acetamide, 2-(cyclopropylamino)-N-[4-(2-phenylethynyl)-phenyl]-acetamide, 2-(ethylamino)-N-[4-(2-phenylethynyl)phenyl]acetamide, 2-[(2-methyl-propyl)amino]-N-[4-(2-phenylethynyl)phenyl]acetamide, 5-phenyl-2H-benzo-[d]1,3-dioxolene, 2-chloro-1-methoxy-4-phenylbenzene, 2-[(imidazolylmethyl)-amino]-N-[4-(2-phenylethynyl)phenyl]acetamide, 4-phenyl-1-phenoxybenzene, N-(2-amino-ethyl)-[4-(2-phenylethynyl)phenyl]carboxamide, 2-{[(4-fluorophenyl)methyl]-amino}-N-[4-(2-phenylethynyl)phenyl]acetamide, 2-{[(4-methylphenyl)methyl]amino}-N-[4-(2-phenyl-ethynyl)phenyl]acetamide, 4-phenyl-1-(trifluoromethyl)benzene, 1-butyl-4-phenylbenzene, 2-(cyclohexylamino)-N-[4-(2-phenylethynyl)phenyl]acetamide, 2-(ethyl-methyl-amino)-N-[4-(2-phenyl-ethynyl)phenyl]acetamide, 2-(butylamino)-N-[4-(2-phenyl-ethynyl)-phenyl]acetamide, N-[4-(2-phenylethynyl)phenyl]-2-(4-pyridylamino)-acetamide, N-[4-(2-phenylethynyl)phenyl]-2-(quinuclidin-3-ylamino)acetamide, N-[4-(2-phenyl-ethynyl)phenyl]pyrrolidin-2-ylcarboxamide, 2-amino-3-methyl-N-[4-(2-phenyl-ethynyl)-phenyl]butanamide, 4-(4-phenylbuta-1,3-diynyl)phenylamine, 2-(dimethyl-amino)-N-[4-(4-phenylbuta-1,3-diynyl)phenyl]acetamide, 2-(ethylamino)-N-[4-(4-phenylbuta-1,3-diynyl)-phenyl]acetamide, 4-ethyl-1-phenylbenzene, 1-[4-(2-phenyl-ethynyl)-phenyl]ethan-1-one, N-(1-carbamoyl-2-hydroxypropyl)[4-(4-phenylbuta-1,3-diynyl)-phenyl]-carbox-amide, N-[4-(2-phenylethynyl)phenyl]propanamide, 4-methoxy-phenyl phenyl ketone, phenyl-N-benzamide, (tert-butoxy)-N-[(4-phenylphenyl)-methyl]-carboxamide, 2-(3-phenyl-phenoxy)ethanehydroxamic acid, 3-phenylphenyl propanoate, 1-(4-ethoxyphenyl)-4-methoxybenzene, and [4-(2-phenylethynyl)phenyl]pyrrole.

"Heteroarylaryl" refers to a biaryl group where one of the aryl groups is a heteroaryl group. Exemplary heteroarylaryl groups include, for example, 2-phenylpyridine, phenylpyrrole, 3-(2-phenylethynyl)pyridine, phenylpyrazole, 5-(2-phenyl-ethynyl)-1,3-dihydropyrimidine-2,4-dione, 4-phenyl-1,2,3-thiadiazole, 2-(2-phenylethynyl)pyrazine, 2-phenylthiophene, phenylimidazole, 3-(2-piperazinyl-phenyl)-furan, 3-(2,4-dichlorophenyl)-4-methylpyrrole, and the like. Preferred optionally substituted heteroarylaryl groups include: 5-(2-phenylethynyl)pyrimidine-2-ylamine, 1-methoxy-4-(2-thienyl)benzene, 1-methoxy-3-(2-thienyl)benzene, 5-methyl-2-phenyl-pyridine, 5-methyl-3-phenylisoxazole, 2-[3-(trifluoromethyl)phenyl]furan, 3-fluoro-5-(2-furyl)-2-methoxy-1-prop-2-enylbenzene, (hydroxyimino)(5-phenyl(2-thienyl))-methane, 5-[(4-methylpiperazinyl)methyl]-2-phenylthiophene, 2-(4-ethylphenyl)-thio-phene, 4-methyl-thio-1-(2-thienyl)benzene, 2-(3-nitrophenyl)thiophene, (tert-butoxy)-N-[(5-phenyl-(3-pyridyl))methyl]carboxamide, hydroxy-N-[(5-phenyl(3-pyridyl))methyl]-amide, 2-(phenyl-methylthio)pyridine, and benzimidazole.

"Heteroarylheteroaryl" refers to a biaryl group where both of the aryl groups is a heteroaryl group. Exemplary heteroarylheteroaryl groups include, for example, 3-pyridylimidazole, 2-imidazolylpyrazine, and the like. Preferred optionally substituted heteroarylheteroaryl groups include: 2-(4-piperazinyl-3-pyridyl)furan, diethyl-(3-pyrazin-2-yl(4-pyridyl))amine, and dimethyl{2-[2-(5-methylpyrazin-2-yl)ethynyl](4-pyridyl)}amine.

"Optionally substituted" or "substituted" refers to the replacement of hydrogen with one or more monovalent or divalent radical. Suitable substitution groups include, for example, hydroxyl, nitro, amino, imino, cyano, halo, thio, sulfonyl, thioamido, amidino, imidino, oxo, oxamidino, methoxamidino, imidino, guanidino, sulfonamido, carboxyl, formyl, alkyl, substituted alkyl, haloalkyl, alkyamino, haloalkylamino, alkoxy, haloalkoxy, alkoxy-alkyl, alkylcarbonyl, aminocarbonyl, arylcarbonyl, aralkylcarbonyl, heteroarylcarbonyl, heteroaralkyl-carbonyl, alkylthio, aminoalkyl, cyanoalkyl, aryl, benzyl, pyridyl, pyrazolyl, pyrrole, thiophene, imidazolyl, and the like.

The substitution group can itself be substituted. The group substituted onto the substitution group can be carboxyl, halo, nitro, amino, cyano, hydroxyl, alkyl, alkoxy, aminocarbonyl, —SR, thioamido, —SO$_3$H, —SO$_2$R, or cycloalkyl, where R is typically hydrogen, hydroxyl or alkyl.

When the substituted substituent includes a straight chain group, the substitution can occur either within the chain (e.g., 2-hydroxypropyl, 2-aminobutyl, and the like) or at the chain terminus (e.g., 2-hydroxyethyl, 3-cyanopropyl, and the like). Substituted substituents can be straight chain, branched or cyclic arrangements of covalently bonded carbon or heteroatoms.

Representative substituted aminocarbonyl groups include, for example, those shown below. These can be further substituted by heterocyclyl groups and heteroaryl groups as will be apparent to those having skill in the organic and medicinal chemistry arts in conjunction with the disclosure herein. Preferred aminocarbonyl groups include: N-(2-cyanoethyl)carboxamide, N-(3-methoxypropyl)carboxamide, N-cyclopropylcarboxamide, N-(2-hydroxy-isopropyl)carboxamide, methyl 2-carbonylamino-3-hydroxypropanoate, N-(2-hydroxypropyl)carboxamide, N-(2-hydroxy-isopropyl)carboxamide, N-[2-hydroxy-1-(hydroxymethyl)ethyl]carboxamide, N-(2-carbonylaminoethyl)acetamide, N-(2-(2-pyridyl)ethyl)carboxamide, N-(2-pyridylmethyl)carboxamide, N-(oxolan-2-ylmethyl)-carboxamide, N-(4-hydroxypyrrolidin-2-yl)carboxamide, N-[2-(2-hydroxyethoxy)ethyl]-carboxamide, N-(4-hydroxycyclohexyl)carboxamide, N-[2-(2-oxo-4-imidazolinyl)ethyl]-carboxamide, N-(carbonylaminomethyl)acetamide, N-(3-pyrrolidinylpropyl)carboxamide, N-[1-(carbonylaminomethyl)pyrrolidin-3-yl]acetamide, N-(2-morpholin-4-ylethyl)carboxamide, N-[3-(2-oxopyrrolidinyl)propyl]carboxamide, 4-methyl-2-oxopiperazinecarbaldehyde, N-(2-hydroxy-3-pyrrolidinylpropyl)carboxamide, N-(2-hydroxy-3-morpholin-4-ylpropyl)carboxamide, N-{2-[(5-cyano-2-pyridyl)amino]ethyl}carboxamide, 3-(dimethyl-amino)pyrrolidinecarbaldehyde, N-[(5-methylpyrazin-2-yl)methyl]carboxamide, 2,2,2-trifluoro-N-(1-formylpyrrolidin-3-yl)acetamide,

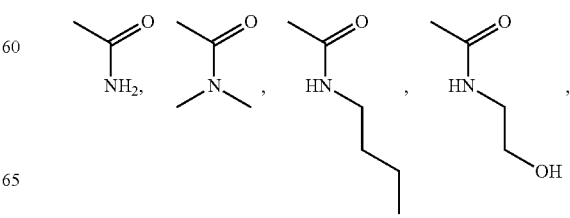

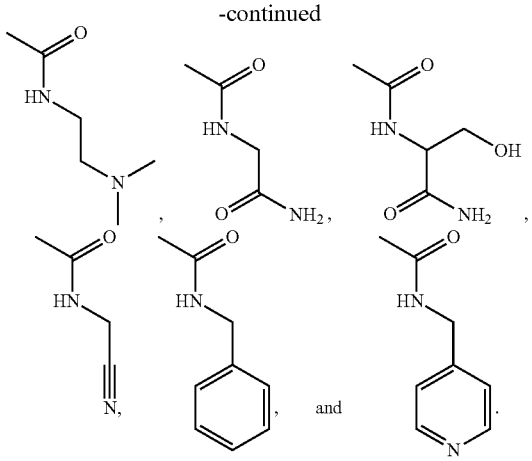

Representative substituted alkoxycarbonyl groups include, for example, those shown below. These alkoxycarbonyl groups can be further substituted as will be apparent to those having skill in the organic and medicinal chemistry arts in conjunction with the disclosure herein.

Representative substituted alkoxycarbonyl groups include, for example, those shown below. These alkoxycarbonyl groups can be further substituted as will be apparent to those having skill in the organic and medicinal chemistry arts in conjunction with the disclosure herein.

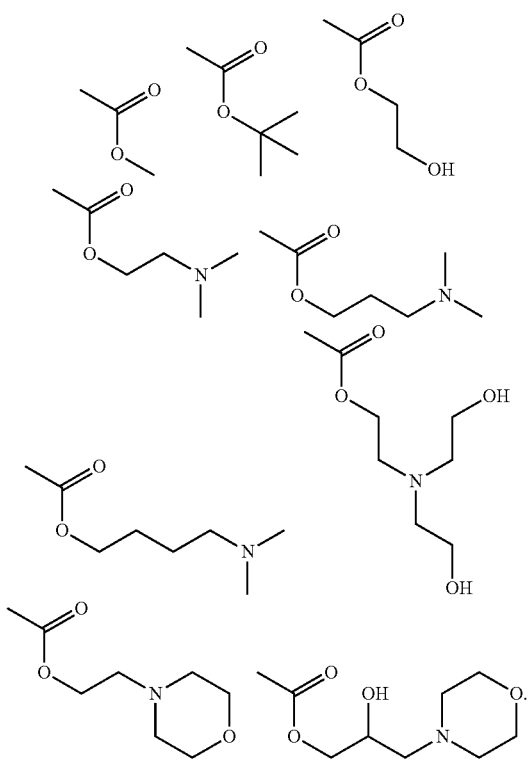

The term "protected" with respect to hydroxyl groups, amine groups, and sulfhydryl groups refers to forms of these functionalities which are protected from undesirable reaction with a protecting group known to those skilled in the art such as those set forth in *Protective Groups in Organic Synthesis*, Greene, T. W.; Wuts, P. G. M., John Wiley & Sons, New York, N.Y., (3rd Edition, 1999) which can be added or removed using the procedures set forth therein. Examples of protected hydroxyl groups include, but are not limited to, silyl ethers such as those obtained by reaction of a hydroxyl group with a reagent such as, but not limited to, t-butyldimethyl-chlorosilane, trimethylchlorosilane, triisopropylchlorosilane, triethylchlorosilane; substituted methyl and ethyl ethers such as, but not limited to methoxymethyl ether, methylthiomethyl ether, benzyloxymethyl ether, t-butoxymethyl ether, 2-methoxyethoxymethyl ether, tetrahydropyranyl ethers, 1-ethoxyethyl ether, allyl ether, benzyl ether; esters such as, but not limited to, benzoylformate, formate, acetate, trichloroacetate, and trifluoroacetate. Examples of protected amine groups include, but are not limited to, amides such as, formamide, acetamide, trifluoroacetamide, and benzamide; imides, such as phthalimide, and dithiosuccinimide; and others. Examples of protected sulfhydryl groups include, but are not limited to, thioethers such as S-benzyl thioether, and S-4-picolyl thioether; substituted S-methyl derivatives such as hemithio, dithio and aminothio acetals; and others.

"Carboxy-protecting group" refers to a carbonyl group which has been esterified with one of the commonly used carboxylic acid protecting ester groups employed to block or protect the carboxylic acid function while reactions involving other functional sites of the compound are carried out. In addition, a carboxy protecting group can be attached to a solid support whereby the compound remains connected to the solid support as the carboxylate until cleaved by hydrolytic methods to release the corresponding free acid. Representative carboxy-protecting groups include, for example, alkyl esters, secondary amides and the like.

The term "pharmaceutical composition" is defined herein to refer to a mixture or solution containing at least one therapeutic agent to be administered to a human patient, in order to prevent or treat a particular disease or condition affecting the human patient.

The term "pharmaceutically acceptable" is defined herein to refer to those compounds, materials, compositions and/or dosage forms, which are, within the scope of sound medical judgment, suitable for contact with the tissues a human patient without excessive toxicity, irritation allergic response and other problem complications commensurate with a reasonable benefit/risk ratio.

The term "treating" or "treatment" as used herein comprises a treatment relieving, reducing or alleviating at least one symptom in a human patient or effecting a delay of progression of a disease. For example, treatment can be the diminishment of one or several symptoms of a disorder or complete eradication of a disorder, such as cancer. Within the meaning of the present invention, the term "treat" also denotes to arrest, delay the onset (i.e., the period prior to clinical manifestation of a disease) and/or reduce the risk of developing or worsening a disease. The term "protect" is used herein to mean prevent delay or treat, or all, as appropriate, development or continuance or aggravation of a disease in a subject.

The term "prevent", "preventing" or "prevention" as used herein comprises the prevention of at least one symptom associated with or caused by the state, disease or disorder being prevented.

The term "pharmaceutically effective amount" or "clinically effective amount" of a combination of therapeutic agents is an amount sufficient to provide an observable improvement over the baseline clinically observable signs and symptoms of the disorder treated with the combination.

The phrase "a human patient in need of such treatment" as used herein refers to a human patient diagnosed with or suffering from the identified proliferative disease.

The term about" or "approximately" shall have the meaning of within 10%, more preferably within 5%, of a given value or range.

WO07/084,786 describes pyrimidine derivatives, which have been found to inhibit the activity of phosphatidylinositol 3-kinase (PI3K). Specific phosphatidylinositol 3-kinase (PI3K) inhibitors suitable for the present invention, their preparation and suitable pharmaceutical formulations containing the same are described in WO07/084,786 and include compounds of formula (I):

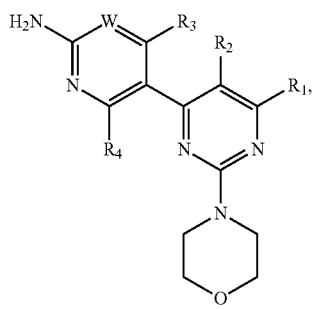

wherein W is $CR_w$ or N, wherein
$R_w$ is selected from the group consisting of:
(1) hydrogen,
(2) cyano,
(3) halogen,
(4) methyl,
5) trifluoromethyl,
(6) sulfonamide;
$R_1$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{1a}$,
(13) —$CO_2R_{1a}$,
(14) —$CONR_{1a}R_{1b}$,
(15) —$NR_{1a}R_{1b}$,
(16) —$NR_{1a}COR_{1b}$,
(17) —$NR_{1a}SO_2R_{1b}$,
(18) —$OCOR_{1a}$,
(19) —$OR_{1a}$,
(20) —$SR_{1a}$,
(21) —$SOR_{1a}$,
(23) —$SO_2NR_{1a}R_{1b}$ wherein
$R_{1a}$, and $R_{1b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl;

$R_2$ is selected from the group consisting of:
(1) hydrogen,
(2) cyano,
(3) nitro,
(4) halogen,
(5) hydroxy,
(6) amino,
(7) substituted and unsubstituted alkyl,
(8) —$COR_{2a}$, and
(9) —$NR_{2a}COR_{2b}$, wherein
$R_{2a}$, and $R_{2b}$ are independently selected from the group consisting of:
(a) hydrogen, and
(b) substituted or unsubstituted alkyl;
$R_3$ is selected from the group consisting of:
(1) hydrogen,
(2) cyano,
(3) nitro,
(4) halogen,
(5) substituted and unsubstituted alkyl,
(6) substituted and unsubstituted alkenyl,
(7) substituted and unsubstituted alkynyl,
(8) substituted and unsubstituted aryl,
(9) substituted and unsubstituted heteroaryl,
(10) substituted and unsubstituted heterocyclyl,
(11) substituted and unsubstituted cycloalkyl,
(12) —$COR_{3a}$,
(14) —$NR_{3a}R_{3b}$,
(13) —$NR_{3a}COR_{3b}$,
(15) —$NR_{3a}SO_2R_{3b}$,
(16) —$OR_{3a}$,
(17) —$SR_{3a}$,
(18) —$SOR_{3a}$,
(19) —$SO_2R_{3a}$, wherein
$R_{3a}$, and $R_{3b}$ are independently selected from the group consisting of:
(a) hydrogen,
(b) substituted or unsubstituted alkyl,
(c) substituted and unsubstituted aryl,
(d) substituted and unsubstituted heteroaryl,
(e) substituted and unsubstituted heterocyclyl, and
(f) substituted and unsubstituted cycloalkyl; and
$R_4$ is selected from the group consisting of
(1) hydrogen, and
(2) halogen.

The radicals and symbols as used in the definition of a compound of formula (I) have meanings as disclosed in WO07/084,786 which publication is hereby incorporated into the present application by reference.

The phosphatidylinositol 3-kinase inhibitor compound of formula (I) may be present in the combination in the form of the free base or a pharmaceutically acceptable salt thereof. Such salts can be prepared in situ during the final isolation and purification of the compounds, or by separately reacting the base or acid functions with a suitable organic or inorganic acid or base, respectively. Suitable salts of the compound of formula (I) include but are not limited to the following: acetate, adipate, alginate, citrate, aspartate, benzoate, benzenesulfonate, bisulfate, butyrate, camphorate, camphorsulfonate, digluconate, cyclopentanepropionate, dodecylsulfate, ethanesulfonate, glucoheptanoate, glycerophosphate, hemi-sulfate, heptanoate, hexanoate, fumarate, hydrochloride, hydrobromide, hydroiodide, 2 hydroxyethanesulfonate, lactate, maleate, methanesulfonate, nicotinate, 2 naphth-alenesulfonate, oxalate, pamoate, pectinate, persulfate, 3 phenylproionate, picrate, pivalate, propionate, succinate, sulfate, tartrate, thiocyanate, p toluenesulfonate, and undecanoate. Also, the basic nitrogen-containing groups can be quaternized with such agents as alkyl halides, such as methyl, ethyl, propyl, and butyl chloride, bromides, and iodides; dialkyl sulfates like dimethyl, diethyl, dibutyl, and diamyl sulfates, long chain halides such as decyl, lauryl, myristyl, and stearyl chlorides, bromides and iodides, aralkyl halides like benzyl and phenethyl bromides, and others.

Examples of acids that may be employed to form pharmaceutically acceptable acid addition salts include such inorganic acids as hydrochloric acid, hydroboric acid, nitric acid, sulfuric acid and phosphoric acid and such organic acids as formic acid, acetic acid, trifluoroacetic acid, fumaric acid, tartaric acid, oxalic acid, maleic acid, methanesulfonic acid, succinic acid, malic acid, methanesulfonic acid, benzenesulfonic acid, and p toluenesulfonic acid, citric acid, and acidic amino acids such as aspartic acid and glutamic acid.

Pharmaceutically acceptable salts include, but are not limited to, cations based on the alkali and alkaline earth metals, such as sodium, lithium, potassium, calcium, magnesium, aluminum salts and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. Other representative organic amines useful for the formation of base addition salts include diethylamine, ethylenediamine, ethanolamine, diethanolamine, piperazine, pyridine, picoline, triethanolamine and the like, and basic amino acids such as arginine, lysine and ornithine.

A preferred compound of formula (I) for use in the combination of the present invention is the phosphatidylinositol 3-kinase (PI3K) inhibitor 5-(2,6-di-morpholin-4-yl-pyrimidin-4-yl)-4-trifluoromethyl-pyridin-2-ylamine (hereinafter "COMPOUND A") or its hydrochloride salt. The synthesis of COMPOUND A is described in WO 2007/084786 as Example 10, the contents of which are incorporated herein by reference.

In accordance with the present invention, the compounds of formula (I) or a pharmaceutically acceptable salt thereof, alone or in combination with one additional therapeutic agent, may be used for the treatment of a proliferative disease, particularly cancer. The term "cancer" refers to cancer diseases that can be beneficially treated by the inhibition of PI3K, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; head and neck; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

The compounds of the present invention are useful in pharmaceutical compositions for human or veterinary use where inhibition of PI3K is indicated, for example, in the treatment of proliferative diseases such as tumor and/or cancerous cell growth mediated by PI3K. In particular, the compounds are useful in the treatment of human cancers, including, for example, lung and bronchus; prostate; breast; pancreas; colon and rectum; thyroid; liver and intrahepatic bile duct; hepatocellular; gastric; glioma/glioblastoma; endometrial; melanoma; kidney and renal pelvis; urinary bladder; uterine corpus; uterine cervix; ovary; head and neck; multiple myeloma; esophagus; acute myelogenous leukemia; chronic myelogenous leukemia; lymphocytic leukemia; myeloid leukemia; brain; oral cavity and pharynx; larynx; small intestine; non-Hodgkin lymphoma; melanoma; and villous colon adenoma.

In the preferred embodiment, the compound of formula (I) or a pharmaceutically acceptable salt thereof may be used for the treatment of a cancer selected from lung and bronchus, prostate, breast, pancreas, colon and rectum, liver and intrahepatic bile duct, hepatocellular, gastric, glioma/glioblastoma, and endometrial.

For purposes of the present invention, the compound of formula (I) or a pharmaceutically acceptable salt thereof may be administered at a dosage of about 60 to about 120 mg per day to a human patient in need thereof. The total daily dose may be administered to the human patient in single or divided doses. Dosage unit compositions may contain such amounts of submultiples thereof to make up the daily dose. In general, treatment regimens according to the present invention comprise administration to a patient in need of such treatment from about 60 mg to about 120 mg of the compound(s) of this invention per day in single or multiple doses. In accordance with the present invention, the compound of formula (I) is administered to a human patient in need thereof at a dosage of about 60 to about 120 mg daily for five consecutive days in any seven day period. In the preferred embodiment, the compound of formula (I) or a pharmaceutically acceptable salt thereof is administered at dosage of about 100 mg daily for five consecutive days in any seven day period.

The phrase "five consecutive days in any seven day period" is intended to refer to the daily dosage of the compound of formula (I) or a pharmaceutically acceptable salt thereof is administered for five consecutive days in any seven day period. Thus, in any cycle, a human patient is administered an amount of about 60 to about 120 mg of the compound of formula (I) or a pharmaceutically acceptable salt thereof each day (daily) for five consecutive days and then not administered any compound of formula (I) or a pharmaceutically acceptable salt thereof for two consecutive days before receiving any further doses of said compound.

In the preferred embodiment, the compound of formula (I) is 5-(2,6-di-morpholin-4-yl-pyrimidin-4-yl)-4-trifluoromethyl-pyridin-2-ylamine (hereinafter "COMPOUND A") or a pharmaceutically acceptable salt thereof which is administered orally at dosage of about 100 mg daily for five consecutive days in any seven day period.

It is discovered that reduction of the weekly dosing of the compound of formula (I) or a pharmaceutically acceptable salt thereof from about 60 to about 120 mg daily (i.e., 7 days per week) to about 60 to about 120 mg daily for five consecutive days in any seven day period is effective to treat a proliferative disorder in human patient in need thereof while relieving, reducing, or alleviating negative side effects. Examples of such negative side effects include neutropenia, thrombocytopenia, serum creatine (e.g., 2-3× ULN, or >3.0-6.0×ULN or >6.0×ULN), elevated bilirubin, asymptomatic amylase and/or lipase elevation (e.g, CTCAE Grade 3 (>2.0-5.0×ULN) or Grade 4 (>5.0×ULN)), mood alteration (e.g., CTCAE Grade 2, 3, or 4), neurotoxicity (e.g, ≥1 CTCAE Grade level Increase), hyperglycemia, rash, diarrhea (e.g., CTCAE Grade 2, 3 or 4), anorexia, nausea, fatigue (e.g. CTCAE Grade 3 or 4), pneumonitis (e.g, CTCAE Grade 2, 3 or 4), pruritus and mucositis. It is understood by one of ordinary skill in the art how to assess such negative side effects in a patient suffering from proliferative diseases, for example, by assessing such patient using the NCI Common Toxicity Criteria for Adverse Effects, version 3.0 (http://ctep.cancer.gov/forms/CTCAEv3.pdf), which is hereby incorporated by reference in its entirety.

Thus, in one aspect, the invention relates to a method of treating a proliferative disease in a patient in need thereof comprising first administering to such human patient in need thereof a compound of formula (I) or a pharmaceutically acceptable salt thereof in amount of about 60 to about 120 mg daily, second determining said patient has a condition selected from neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis after administration of the compound of formula (I) or a pharmaceutically acceptable salt thereof after administration of about 60 to about 120 mg daily to said human patient, and third reducing the dosage of the compound of formula (I) or a pharmaceutically acceptable salt thereof to about 60 to about 120 mg daily for five consecutive days in any seven day period.

In a preferred embodiment, the human patient is administered 100 mg daily of the compound of formula (I) or a pharmaceutically acceptable salt thereof for five consecutive days in any seven day period.

In a further embodiment, the invention relates to a method of treating a proliferative disease comprising first administering to a human patient in need thereof a compound of formula (I) or a pharmaceutically acceptable salt thereof in an amount of about 60 to about 120 mg daily, second determining said patient has a condition selected from neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis after administration of the compound of formula (I) or a pharmaceutically acceptable salt thereof after administration of about 60 to about 120 mg daily to said human patient, and third reducing the dosage of the compound of formula (I) or a pharmaceutically acceptable salt thereof to about 60 to about 120 mg daily for five consecutive days in any seven day period, wherein the condition selected from neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis is alleviated or treated.

Use of a compound of formula (I) or a pharmaceutically acceptable salt thereof in the preparation of a medicament for use in the treatment of a proliferative disease wherein the medicament comprising a therapeutically effective dose of about 60 to about 120 mg of compound of formula (I) is administered to a human patient in need thereof for five consecutive days in any seven day period.

Use of a compound of formula (I) or a pharmaceutically acceptable salt thereof for use in the treatment of a proliferative disease comprising administering a compound of formula (I) or a pharmaceutically acceptable salt thereof in a therapeutically effective dosage of about 60 to about 120 mg of compound of formula (I) or a pharmaceutically acceptable salt thereof for five consecutive days in any seven day period.

Use of a compound of formula (I) or a pharmaceutically acceptable salt thereof for use in any method set forth above.

A compound of formula (I) or a pharmaceutically acceptable salt thereof for use in the treatment of a proliferative disease wherein the compound of formula (I) or a pharmaceutically acceptable salt thereof is administered at a therapeutically effective dosage of about 60 to about 120 mg for five consecutive days in any seven day period.

A compound of formula (I) or a pharmaceutically acceptable salt thereof for use in any method set forth above.

A therapeutic regimen comprising administering a compound of formula (I) or a pharmaceutically acceptable salt thereof in an therapeutically effective amount of about 60 to about 120 mg of compound of formula (I) or a pharmaceutically acceptable salt thereof for five consecutive days in any seven day period and wherein the compound of formula (I) or a pharmaceutically acceptable salt thereof is administered in combination with at least one additional therapeutic agent.

Anticancer agents for use with the invention include, but are not limited to, one or more of the following set forth below:

A. Kinase Inhibitors: Kinase inhibitors for use as anticancer agents in conjunction with the compositions of the present invention include inhibitors of Epidermal Growth Factor Receptor (EGFR) kinases such as small molecule quinazolines, for example gefitinib (U.S. Pat. No. 5,457,105, U.S. Pat. No. 5,616,582, and U.S. Pat. No. 5,770,599), ZD-6474 (WO 01/32651), erlotinib (Tarceva®, U.S. Pat. No. 5,747,498 and WO 96/30347), and lapatinib (U.S. Pat. No. 6,727,256 and WO 02/02552); Vascular Endothelial Growth Factor Receptor (VEGFR) kinase inhibitors, including SU-11248 (WO 01/60814), SU 5416 (U.S. Pat. No. 5,883,113 and WO 99/61422), SU 6668 (U.S. Pat. No. 5,883,113 and WO 99/61422), CHIR-258 (U.S. Pat. No. 6,605,617 and U.S. Pat. No. 6,774,237), vatalanib or PTK-787 (U.S. Pat. No. 6,258,812), VEGF-Trap (WO 02/57423), B43-Genistein (WO-09606116), fenretinide (retinoic acid p-hydroxyphenylamine) (U.S. Pat. No. 4,323,581), IM-862 (WO 02/62826), bevacizumab or Avastin® (WO 94/10202), KRN-951, 3-[5-(methylsulfonylpiperadine methyl)-indolyl]-quinolone, AG-13736 and AG-13925, pyrrolo[2,1-f][1,2,4]triazines, ZK-304709, Veglin®, VMDA-3601, EG-004, CEP-701 (U.S. Pat. No. 5,621,100), Cand5 (WO 04/09769); Erb2 tyrosine kinase inhibitors such as pertuzumab (WO 01/00245), trastuzumab, and rituximab; Akt protein kinase inhibitors, such as RX-0201; Protein Kinase C (PKC) inhibitors, such as LY-317615 (WO 95/17182), and perifosine (US 2003171303); Raf/Map/MEK/Ras kinase inhibitors including sorafenib (BAY 43-9006), ARQ-350RP, LErafAON, BMS-354825 AMG-548, and others disclosed in WO 03/82272; Fibroblast Growth Factor Receptor (FGFR) kinase inhibitors; Cell Dependent Kinase (CDK) inhibitors, including CYC-202 or roscovitine (WO 97/20842 and WO 99/02162); Platelet-Derived Growth Factor Receptor (PGFR) kinase inhibitors such as CHIR-258, 3G3 mAb, AG-13736, SU-11248 and SU6668; Bcr-Abl kinase inhibitors and fusion proteins such as STI-571 or Gleevec® (imatinib); mTOR kinase inhibitors such as everolimus.

B. Anti-Estrogens: Estrogen-targeting agents for use in anticancer therapy in conjunction with the compositions of the present invention include Selective Estrogen Receptor Modulators (SERMs) including tamoxifen, toremifene, raloxifene; aromatase inhibitors including Arimidex® or anastrozole; letrozole; Estrogen Receptor Downregulators (ERDs) including Faslodex® or fulvestrant.

C. Anti-Androgens: Androgen-targeting agents for use in anticancer therapy in conjunction with the compositions of the present invention include flutamide, bicalutamide, finasteride, aminoglutethamide, ketoconazole, and corticosteroids.

D. Other Inhibitors: Other inhibitors for use as anticancer agents in conjunction with the compositions of the present invention include protein farnesyl transferase inhibitors including tipifarnib or R-115777 (US 2003134846 and WO 97/21701), BMS-214662, AZD-3409, and FTI-277; topoisomerase inhibitors including merbarone and diflomotecan (BN-80915); mitotic kinesin spindle protein (KSP) inhibitors including SB-743921 and MKI-833; protease modulators such as bortezomib or Velcade® (U.S. Pat. No. 5,780,454), XL-784; and cyclooxygenase 2 (COX-2) inhibitors including non-steroidal antiinflammatory drugs I (NSAIDs).

E. Cancer Chemotherapeutic Drugs: Particular cancer chemotherapeutic agents for use as anticancer agents in conjunction with the compositions of the present invention include anastrozole (Arimidex®), bicalutamide (Casodex®), bleomycin sulfate (Blenoxane®), busulfan (Myleran®), busulfan injection (Busulfex®), capecitabine (Xeloda®), N4-pentoxycarbonyl-5-deoxy-5-fluorocytidine, carboplatin (Paraplatin®), carmustine (BiCNU®), chlorambucil (Leukeran®), cisplatin (Platinol®), cladribine (Leustatin®), cyclophosphamide (Cytoxan® or Neosar®), cytarabine, cytosine arabinoside (Cytosar-U®), cytarabine liposome injection (DepoCyt®), dacarbazine (DTIC-Dome®), dactinomycin (Actinomycin D, Cosmegan), daunorubicin hydrochloride (Cerubidine®), daunorubicin citrate liposome injection (DaunoXome®), dexamethasone, docetaxel (Taxotere®, US 2004073044), doxorubicin hydrochloride (Adriamycin®, Rubex®), etoposide (Vepesid®), fludarabine phosphate (Fludara®), 5-fluorouracil (Adrucil®, Efudex®), flutamide (Eulexin®), tezacitibine, Gemcitabine (difluorodeoxycitidine), hydroxyurea (Hydrea®), Idarubicin (Idamycin®), ifosfamide (IFEX®), irinotecan (Camptosar®), L-asparaginase (ELSPAR®), leucovorin calcium, melphalan (Alkeran®), 6-mercaptopurine (Purinethol®), methotrexate (Folex®), mitoxantrone (Novantrone®), mylotarg, paclitaxel (Taxon), phoenix (Yttrium90/MX-DTPA), pentostatin, polifeprosan 20 with carmustine implant (Gliadel®), tamoxifen citrate (Nolvadex®), teniposide (Vumon®), 6-thioguanine, thiotepa, tirapazamine (Tirazone®), topotecan hydrochloride for injection (Hycamptin®), vinblastine (Velban®), vincristine (Oncovin®), and vinorelbine (Navelbine®).

F. Alkylating Agents: Alkylating agents for use in conjunction with the compositions of the present invention for anticancer therapeutics include VNP-40101M or cloretizine, oxaliplatin (U.S. Pat. No. 4,169,846, WO 03/24978 and WO 03/04505), glufosfamide, mafosfamide, etopophos (U.S. Pat. No. 5,041,424), prednimustine; treosulfan; busulfan; irofluven (acylfulvene); penclomedine; pyrazoloacridine (PD-115934); 06-benzylguanine; decitabine (5-aza-2-deoxycytidine); brostallicin; mitomycin C (MitoExtra); TLK-286 (Telcyta®); temozolomide; trabectedin (U.S. Pat. No. 5,478,932); AP-5280 (Platinate formulation of Cisplatin); porfiromycin; and clearazide (meclorethamine).

G. Chelating Agents: Chelating agents for use in conjunction with the compositions of the present invention for anticancer therapeutics include tetrathiomolybdate (WO 01/60814); RP-697; Chimeric T84.66 (cT84.66); gadofosveset (Vasovist®); deferoxamine; and bleomycin optionally in combination with electorporation (EPT).

H. Biological Response Modifiers: Biological response modifiers, such as immune modulators, for use in conjunction with the compositions of the present invention for anticancer therapeutics include staurosprine and macrocyclic analogs thereof, including UCN-01, CEP-701 and midostaurin (see WO 02/30941, WO 97/07081, WO 89/07105, U.S. Pat. No. 5,621,100, WO 93/07153, WO 01/04125, WO 02/30941, WO 93/08809, WO 94/06799, WO 00/27422, WO 96/13506 and WO 88/07045); squalamine (WO 01/79255); DA-9601 (WO 98/04541 and U.S. Pat. No. 6,025,387); alemtuzumab; interferons (e.g. IFN-a, IFN-b etc.); interleukins, specifically IL-2 or aldesleukin as well as IL-1, IL-3, IL-4, IL-5, IL-6, IL-7, IL-8, IL-9, IL-10, IL-11, IL-12, and active biological variants thereof having amino acid sequences greater than 70% of the native human sequence; altretamine (Hexylen®); SU 101 or leflunomide (WO 04/06834 and U.S. Pat. No. 6,331,555); imidazoquinolines such as resiquimod and imiquimod (U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612); and SMIPs, including benzazoles, anthraquinones, thiosemicarbazones, and tryptanthrins (WO 04/87153, WO 04/64759, and WO 04/60308).

I. Cancer Vaccines: Anticancer vaccines for use in conjunction with the compositions of the present invention include Avicine® (Tetrahedron Letters 26, 1974 2269-70); oregovomab (OvaRex®); Theratope® (STn-KLH); Melanoma Vaccines; GI-4000 series (GI-4014, GI-4015, and GI-4016), which are directed to five mutations in the Ras protein; GlioVax-1; MelaVax; Advexin® or INGN-201 (WO 95/12660); Sig/E7/LAMP-1, encoding HPV-16 E7; MAGE-3 Vaccine or M3TK (WO 94/05304); HER-2VAX; ACTIVE, which stimulates T-cells specific for tumors; GM-CSF cancer vaccine; and *Listeria monocytogenes*-based vaccines.

J. Antisense Therapy: Anticancer agents for use in conjunction with the compositions of the present invention also include antisense compositions, such as AEG-35156 (GEM-640); AP-12009 and AP-11014 (TGF-beta2-specific antisense oligonucleotides); AVI-4126; AVI-4557; AVI-4472; oblimersen (Genasense®); JFS2; aprinocarsen (WO 97/29780); GTI-2040 (R2 ribonucleotide reductase mRNA antisense oligo) (WO 98/05769); GTI-2501 (WO 98/05769); liposome-encapsulated c-Raf antisense oligodeoxynucleotides (LErafAON) (WO 98/43095); and Sirna-027 (RNAi-based therapeutic targeting VEGFR-1 mRNA).

The structure of the drug substances identified by code numbers, generic or trade names may be taken from the Internet, actual edition of the standard compendium "The Merck Index" or from databases, e.g., Patents International, e.g., IMS World Publications, or the publications mentioned above and below. The corresponding content thereof is hereby incorporated by reference.

Examples of proliferative diseases that may be treated with a combination of a compound of formula (I) or a pharmaceutically acceptable salt thereof and at least one additional therapeutic agent include, but not limited to, those set forth above. In the combination of the present invention, the compound of formula (I) or a pharmaceutically acceptable salt thereof is administered at a dosage of about 60 mg to about 120 mg, preferably 100 mg, daily for five consecutive days in any seven day period.

The administration of said combination may result not only in a beneficial effect, e.g. therapeutic effect as compared to either monotherapy, e.g, a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit is that lower doses of the active ingredients of said combination can be used, for example, that the dosages need not only often be smaller, but are also applied less frequently, or can be used in order to diminish the incidence of side-effects observed with one of the combination partners alone. This is in accordance with the desires and requirements of the patients to be treated.

It can be shown by established test models that the combination of the invention results in the beneficial effects described herein before. The person skilled in the art is fully enabled to select a relevant test model to prove such beneficial effects. The pharmacological activity of a combination of the invention may, for example, be demonstrated in a clinical study or in a test procedure as essentially described hereinafter.

Suitable clinical studies are in particular, for example, open label, dose escalation studies in patients with a proliferative disease, including for example a tumor disease, e.g., breast cancer. Such studies prove in particular the synergism of the therapeutic agents of the combination of the invention. The beneficial effects on a proliferative disease may be determined directly through the results of these studies which are known as such to a person skilled in the art. Such studies may be, in particular, be suitable to compare the effects of a monotherapy using the therapeutic agents and a combination of the invention. In one embodiment, the dose of the phosphatidylinositol 3-kinase inhibitor compound of formula (I), e.g., COMPOUND A, is escalated until the Maximum Tolerated Dosage is reached, and the combination partner is administered with a fixed dose. Alternatively, phosphatidylinositol 3-kinase inhibitor compound of formula (I), e.g., COMPOUND A, may be administered in a fixed dose and the dose of the combination partner may be escalated. Each patient may receive doses of the phosphatidylinositol 3-kinase inhibitor either daily or intermittently. The efficacy of the treatment may be determined in such studies, e.g., after 12, 18 or 24 weeks by evaluation of symptom scores every 6 weeks.

A pharmaceutical composition for use in the treatment of a proliferative disease in a human patient in need thereof comprising a therapeutically effective amount of about 60 to about 120 mg of a compound of formula (I) or pharmaceutically acceptable salt thereof together with one or more pharmaceutically acceptable excipients which is administered for five consecutive days in any seven day period.

A pharmaceutical composition comprising a compound of formula (I) or a pharmaceutically acceptable salt thereof, alone or in combination with at least one additional therapeutic agent (i.e., combination partner), for enteral or parenteral administration are, for example, those in unit dosage forms, such as sugar-coated tablets, tablets, capsules or suppositories, or ampoules. If not indicated otherwise, these are prepared in a manner known per se, for example by means of various conventional mixing, comminution, granulating, sugar-coating, dissolving, lyophilizing processes, or fabrication techniques readily apparent to those skilled in the art.

A unit dosage form containing the compound of formula (I) or a pharmaceutically acceptable salt thereof, alone or in combination with at least one additional therapeutic agent, may be in the form of micro-tablets enclosed inside a capsule, e.g. a gelatin capsule. For this, a gelatin capsule as is employed in pharmaceutical formulations can be used, such as the hard gelatin capsule known as CAPSUGEL, available from Pfizer.

Pharmaceutical compositions of the present invention may optionally further comprise additional conventional carriers or excipients used for pharmaceuticals. Examples of such carriers include, but are not limited to, disintegrants, binders, lubricants, glidants, stabilizers, and fillers, diluents, colorants, flavours and preservatives. One of ordinary skill in the art may select one or more of the aforementioned carriers with respect to the particular desired properties of the dosage form by routine experimentation and without any undue burden. The amount of each carriers used may vary within ranges conventional in the art. The following references which are all hereby incorporated by reference disclose techniques and excipients used to formulate oral dosage forms. See The Handbook of Pharmaceutical Excipients, 4th edition, Rowe et al., Eds., American Pharmaceuticals Association (2003); and Remington: the Science and Practice of Pharmacy, 20th edition, Gennaro, Ed., Lippincott Williams & Wilkins (2003).

These optional additional conventional carriers may be incorporated into the oral dosage form either by incorporating the one or more conventional carriers into the initial mixture before or during melt granulation or by combining the one or more conventional carriers with the granules in the oral dosage form. In the latter embodiment, the combined mixture may be further blended, e.g., through a V-blender, and subsequently compressed or molded into a tablet, for example a monolithic tablet, encapsulated by a capsule, or filled into a sachet.

Examples of pharmaceutically acceptable disintegrants include, but are not limited to, starches; clays; celluloses; alginates; gums; cross-linked polymers, e.g., cross-linked polyvinyl pyrrolidone or crospovidone, e.g., POLYPLASDONE XL from International Specialty Products (Wayne, N.J.); cross-linked sodium carboxymethylcellulose or croscarmellose sodium, e.g., AC-DI-SOL from FMC; and cross-linked calcium carboxymethylcellulose; soy polysaccharides; and guar gum. The disintegrant may be present in an amount from about 0% to about 10% by weight of the composition. In one embodiment, the disintegrant is present in an amount from about 0.1% to about 5% by weight of composition.

Examples of pharmaceutically acceptable binders include, but are not limited to, starches; celluloses and derivatives thereof, for example, microcrystalline cellulose, e.g., AVICEL PH from FMC (Philadelphia, Pa.), hydroxypropyl cellulose hydroxyethyl cellulose and hydroxylpropylmethyl cellulose METHOCEL from Dow Chemical Corp. (Midland, Mich.); sucrose; dextrose; corn syrup; polysaccharides; and gelatin. The binder may be present in an amount from about 0% to about 50%, e.g., 2-20% by weight of the composition.

Examples of pharmaceutically acceptable lubricants and pharmaceutically acceptable glidants include, but are not limited to, colloidal silica, magnesium trisilicate, starches, talc, tribasic calcium phosphate, magnesium stearate, aluminum stearate, calcium stearate, magnesium carbonate, magnesium oxide, polyethylene glycol, powdered cellulose and microcrystalline cellulose. The lubricant may be present in an amount from about 0% to about 10% by weight of the composition. In one embodiment, the lubricant may be present in an amount from about 0.1% to about 1.5% by weight of composition. The glidant may be present in an amount from about 0.1% to about 10% by weight.

Examples of pharmaceutically acceptable fillers and pharmaceutically acceptable diluents include, but are not limited to, confectioner's sugar, compressible sugar, dextrates, dextrin, dextrose, lactose, mannitol, microcrystalline cellulose, powdered cellulose, sorbitol, sucrose and talc. The filler and/or diluent, e.g., may be present in an amount from about 0% to about 80% by weight of the composition.

A package comprising the pharmaceutical composition comprising a compound of formula (I) or a pharmaceutically acceptable salt thereof together with one or more pharmaceutically acceptable pharmaceutically acceptable excipients in combination with instructions to administer said composition in a therapeutically effective amount of about 60 mg to about 120 mg for five consecutive days in any seven day period.

Utility of the dosing regimen of the compounds of formula (I) of the present invention may be demonstrated in vitro, in animal test methods as well as in clinic studies. For example in the utility of the compounds of formula (I) in accordance with the present invention may be demonstrated in accordance with the methods hereinafter described:

Example 1

An open-label clinical study using Compound A or the hydrochloride salt thereof in an initial amount of 100 mg once daily in monotherapy for treatment of patients with advanced solid tumors is investigated.

Patients are initially screened for presence of advanced solid tumors. After screening, patients are administered 100 mg of Compound A or the hydrochloride salt thereof once time each day throughout the clinical study period in an oral dosage form. Patients are administered Compound A or the hydrochloride salt thereof and evaluated by a physician until progression of disease, death, withdrawal of consent or progression free survival for a predetermined time period. During the study period, patients are evaluated for the prevalence of negative side effects selected from neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis. Upon the physician's determination of one or more of these negative side effects at a severity disfavorable to the patient, patients are administered with a modified dosing regimen of Compound A or the hydrochloride salt comprising an amount of about 100 mg of Compound A or the hydrochloride salt daily for five consecutive days in any seven day period until end of the study period. The primary endpoint is progression free survival and response rate.

Example 2

An open-label, randomized multi-institution clinical study using the hydrochloride salt of Compound A alone and in combination with the therapeutic agent letrozole for the treatment of post-menopausal patients with Hormone Receptor Positive (+) metastatic breast cancer is investigated. Patients are evaluated for safety profile/tolerability and preliminary antitumor effect.

Patients are included in the study if they meet the following criteria: at least 18 years of age, ECOG performance status 0-1, suffering from clinical stage 1V invasive mammary carcinoma (ER-positive, or PR-positive) by immunohistochemistry, life expectancy equal to or greater than 6 months, adequate hematologic, hepatic and renal function (ANC≥1500/mm³, platelet count≥100,000 mm³, HgB≥9 g/dL, creatine≤1.5×upper limits of normal, bilirubin≤1.5× upper limits of normal, SGOT, SGPT≤2.5×upper limits of normal if no liver metasis present or SGOT, SGPT alkaline phosphatase≤5×upper limits of normal if liver metasis present, capable of swallowing and retaining oral medication, disease free of prior invasive cancers for >5 years (exception of basal or squamous cancer of skin or cervical carcinoma in situ). Patients may receive concurrent radiation therapy to painful bone metastases or areas of impending bone fracture as long as radiation therapy is completed≤2 weeks prior to study and recovered from toxicity (≤grade 1) induced by this radiation treatment. Post-menopausal female subjects are defined prior to protocol enrollment by any of the following: Subjects at least 55 years of age; Subjects under 55 years of age and amenorrheic for at least 12 months or follicle-stimulating hormone (FSH) values≥IU/L and estradiol levels≤20 IU/L; prior bilateral oophorectomy; prior radiation castration with amenorrhea for at least 6 months; current use of an LHRH agonist for more than 12 months.

Patients are excluded from the study if they have any of the following: locally recurrent resectable breast cancer; pre-menopausal women not on LHRH agonists for more than 12 months prior to study screening, pregnant or lactating women; any malabsorption syndrome significantly affecting gastrointestinal function; history of other malignancy within 5 years prior to enrollment (except subjects with history of completely resectable non-melanoma skin cancer or successfully treated in situ carcinomas); patient with glucose>160 mg/kL or HgBA1c>7.5; concurrent anti-cancer therapy other than the ones specified in the protocol (discontinuing at least 1 week prior to the first dose of study as well as recovered from toxicity to ≤grade 1 (except for alopecia) and at least 2 weeks prior to the study for investigational drugs); prior therapy with a PI3K inhibitor; use of any prohibited concomitant medications; uncontrolled intercurrent illness including but not limited to ongoing or active infection requiring parental antibiotics, impairment of lung function (COPD>grade 2, lung conditions requiring oxygen therapy), symptomatic congestive heart failure (class III or IV or the New York Heart Association classification for heart disease), unstable angina pectoris, angioplasty, stenting or myocardial infarction within 6 months, uncontrolled hypertension (systolic blood pressure>160 mm Hg or diastolic blood pressure>100 mm Hg, fond on two consecutive measurements by a 1 or 2 week period despite adequate medical support), clinically significant cardiac arrhythmia [multifocal premature ventricular contractions, bigeminy, trigeminy, ventricular tachycardia that is symptomatic or requires treatment [National Cancer Institute—Common Terminology Criteria for Adverse Events, Version 4.0, grade 3)], QTcF≥480 msec on screening EKG; ST depression or elevation of ≥1.5 mm in 2 or more leads; diarrhea of any cause≥CTCAE grade 2; psychiatric illness/social situations that would compromise patient safety or limit compliance with study requirements; or patients with symptomatic brain metastases (patients with history of brain metastases must be clinically stable for more than 3 weeks from completion of radiation treatment and 4 weeks from steroid tapering).

Patients with the following mood disorders as judged by investigator or psychiatrist are also excluded: medically documented history of or active major depressive episode; bipolar disorder (I or II), obsessive-compulsive disorder, schizophrenia, a history of suicidal attempt or ideation, or homicidal ideation (immediate risk of doing harm to others); or ≥CTCAE grade 3 anxiety.

In the first stage of the study, safety and tolerability of the hydrochloride salt of Compound A is evaluated in combination with the therapeutic agent letrozole in post-menopausal patients with Hormone Receptor Positive (+) metastatic breast cancer is investigated. The maximum tolerated dose of the hydrochloride salt of Compound A alone is determined at dosages of 100 mg per oral daily, 80 mg per oral daily, and 50 mg per oral daily, in combination with letrozole administered at 2.5 mg/day per oral.

In the second stage of the study, the antitumor effect of the hydrochloride salt of Compound A in combination with letrozole for the treatment of post-menopausal patients with Hormone Receptor Positive (+) metastatic breast cancer is investigated. Patients are administered the hydrochloride salt of Compound A and letrozole at a daily dosage identified to be with in the MTD in the first stage (Arm A).

In one additional experimental arm (Arm C), Patients are administered a daily dosage of the hydrochloride salt of Compound A in the amount of 60, 80 or 100 mg per oral on Monday through Fridays only each week in combination with 2.5 mg/day per oral letrozole.

All patients are evaluated for negative side effects including but not limited to neutropenia, thrombocytopenia, serum creatine, elevated bilirubin, asymptomatic amylase and/or lipase elevation, mood alteration, neurotoxicity, hyperglycemia, rash, diarrhea, anorexia, nausea, fatigue, pneumonitis, pruritus and mucositis.

Secondary outcome for the second stage is progression free survival and response.

Following the above experiment, 51 patients were accrued, 49 progressed after aromatase inhibitor therapy. Median age was 56 years and 95% of patients ad bone metastasis and 70% visceral metastases. The following preliminary results are achieved:

TABLE 1

| | Percentages of Patients | | | | | | | |
|---|---|---|---|---|---|---|---|---|
| | Arm A (20) | | | | Arm C (31) | | | |
| | Grade | | | | Grade | | | |
| Toxicity | 1 | 2 | 3 | Total | 1 | 2 | 3 | Total |
| Hyperglycemia | 50 | 10 | 10 | 70 | 16 | 3 | 0 | 19 |
| Nausea | 55 | 10 | 0 | 65 | 12 | 0 | 0 | 12 |
| Fatigue | 25 | 40 | 5 | 70 | 9 | 3 | 0 | 12 |
| Transaminase elevation | 35 | 25 | 15* | 75 | 16 | 6 | 6 | 16 |
| Diarrhea | 40 | 10 | 0 | 50 | 19 | 0 | 0 | 19 |
| Anxiety | 25 | 15 | 5 | 45 | 3 | 3 | 0 | 6 |
| Depression | 15 | 35 | 5 | 55 | 3 | 6 | 3* | 12 |
| Rash | 30 | 0 | 5 | 35 | 3 | 0 | 0 | 3 |

TABLE 2

| | Patient outcomes | |
|---|---|---|
| | Arm A (20) | Arm C (31) |
| CR | 1 | 0 |
| PR | 1 | 0 |
| SD | 9 | 4 |
| PD | 7 | 8 |
| Non-evaluable | 2 | 5 |
| Still on treatment | 1 | 17 |
| Median TTP (months) | 4 (2-11) | Not reached |
| Discontinued due to toxicity | 6 | 3 |

It has been shown that those patients treated with a dosing regimen of 60, 80 or 100 mg per oral on Monday through Fridays only each week in combination with 2.5 mg/day per oral letrozole had improved side effects or toxicities as compared to those patients receiving dosages of 100 mg per oral daily, 80 mg per oral daily, and 50 mg per oral daily, in combination with letrozole administered at 2.5 mg/day per oral.

What is claimed is:

1. A method of treating breast cancer in a human patient in need of such treatment, comprising administering to said human patient a compound 5-(2,6-di-morpholin-4-yl-pyrimidin-4-yl)-4-trifluoromethyl-pyridin-2-ylamine or a pharmaceutically acceptable salt thereof in a therapeutically effective amount of about 60 to about 120 mg daily for five consecutive days in any seven day period, wherein said compound is administered to the patient each day for five consecutive days and then not administered to the patient for two consecutive days before at least one further dose of said compound is administered to the patient wherein the compound 5-(2,6-di-morpholin-4-yl-pyrimidin-4-yl)-4-trifluoromethyl-pyridin-2-ylamine or a pharmaceutically acceptable salt thereof is administered in combination with letrozole.

2. A method according to claim 1, wherein the compound 5-(2,6-di-morpholin-4-yl-pyrimidin-4-yl)-4-trifluoromethyl-pyridin-2-ylamine or a pharmaceutically acceptable salt thereof is administered in a therapeutically effective amount of about 100 mg daily for five consecutive days in any seven day period.

* * * * *